(12) United States Patent
Loria

(10) Patent No.: US 10,925,718 B2
(45) Date of Patent: Feb. 23, 2021

(54) EXTENSION APPARATUS FOR ARTIFICIAL HAIR IMPLANTS

(71) Applicant: LORIA PRODUCTS LLC, Miami, FL (US)

(72) Inventor: Victor Loria, Miami, FL (US)

(73) Assignee: Loria Products LLC, Miami, FL (US)

( * ) Notice: Subject to any disclaimer, the term of this patent is extended or adjusted under 35 U.S.C. 154(b) by 185 days.

(21) Appl. No.: 16/197,988

(22) Filed: Nov. 21, 2018

(65) Prior Publication Data

US 2019/0117378 A1 Apr. 25, 2019

Related U.S. Application Data

(63) Continuation-in-part of application No. PCT/US2018/044298, filed on Jul. 30, 2018, which is
(Continued)

(51) Int. Cl.
- *A61F 2/10* (2006.01)
- *A41G 5/00* (2006.01)

(52) U.S. Cl.
CPC .............. *A61F 2/10* (2013.01); *A41G 5/008* (2013.01); *A41G 5/0053* (2013.01);
(Continued)

(58) Field of Classification Search
CPC ................... A61F 2/10; A61L 2430/18; A41G 5/004–0046; A41G 5/0053;
(Continued)

(56) References Cited

U.S. PATENT DOCUMENTS

| | | |
|---|---|---|
| 3,596,292 A | 8/1971 | Erb et al. |
| 3,699,969 A | 10/1972 | Allen |

(Continued)

FOREIGN PATENT DOCUMENTS

| | | |
|---|---|---|
| BE | 1017068 | 1/2008 |
| JP | 2014065981 | 4/2014 |

(Continued)

OTHER PUBLICATIONS

International Search Report for related PCT Application No. PCT/US2018/044298 dated Oct. 1, 2018.

(Continued)

*Primary Examiner* — Brian A Dukert
*Assistant Examiner* — Rebecca Lynee Zimmerman
(74) *Attorney, Agent, or Firm* — Caesar Rivise, PC

(57) ABSTRACT

Extension devices for attaching hair extension elements to artificial hair elements that protrude from a subcutaneously implanted hair implant anchor body. One extension device involves a cylindrical structure having respective cavities on opposing ends. One cavity receives the distal end of the artificial hair element while the other cavity receives the hair extension therein. Another extension device involves a hair extension element forming a first portion of the device while a second opposite portion includes a projection that is received inside a hollow interior of the artificial hair element. A third extension device involves a core having a hair extension element projecting from one side of the core while a single cavity is located on a second side, opposite the one side, and which receives the distal end of the artificial implanted hair element therein. The hair extension may comprise ancillary hair elements and bud structures. Ornamental structures may be included on the distal ends of the hair extension element.

11 Claims, 8 Drawing Sheets

Related U.S. Application Data a continuation-in-part of application No. 15/718,637, filed on Sep. 28, 2017, now Pat. No. 10,105,212, which is a continuation-in-part of application No. 15/665,369, filed on Jul. 31, 2017, now Pat. No. 9,993,334, said application No. PCT/US2018/044298 is a continuation-in-part of application No. 15/665,369, filed on Jul. 31, 2017, now Pat. No. 9,993,334.

(52) U.S. Cl.
CPC ............... *A61F 2220/0008* (2013.01); *A61F 2220/0033* (2013.01); *A61F 2230/0069* (2013.01); *A61F 2250/006* (2013.01)

(58) Field of Classification Search
CPC ........ A41G 5/006–0066; A41G 5/0073; A41G 5/008; A41G 5/00; A41G 3/00; A61B 2018/00476
See application file for complete search history.

(56) References Cited

U.S. PATENT DOCUMENTS

| | | | |
|---|---|---|---|
| 5,061,284 A | 10/1991 | Laghi | |
| 5,767,152 A | 6/1998 | Nielsen et al. | |
| 5,800,545 A | 9/1998 | Yamada et al. | |
| 9,492,196 B2 | 11/2016 | Keren et al. | |
| 9,993,334 B1 | 6/2018 | Loria | |
| 10,105,212 B1 | 10/2018 | Loria | |
| 2003/0195625 A1 | 10/2003 | Garci Castro et al. | |
| 2004/0149301 A1 | 8/2004 | Arroyo et al. | |
| 2005/0191748 A1 | 9/2005 | Barrows | |
| 2005/0267506 A1 | 12/2005 | Harris | |
| 2007/0067033 A1* | 3/2007 | Bonati | A61F 2/10 623/15.11 |
| 2007/0282364 A1 | 12/2007 | Haber | |
| 2010/0305699 A1 | 12/2010 | Kim | |
| 2012/0245612 A1 | 9/2012 | Keren et al. | |
| 2016/0345648 A1 | 12/2016 | Miniello et al. | |
| 2017/0099901 A1 | 4/2017 | Lee | |

FOREIGN PATENT DOCUMENTS

| | | |
|---|---|---|
| WO | WO 2006/041265 | 4/2006 |
| WO | WO 2014/196643 | 12/2014 |
| WO | WO 2017/180370 | 10/2017 |
| WO | WO 2019/027864 | 2/2019 |
| WO | WO2019027864 | 2/2019 |

OTHER PUBLICATIONS

Ahdout et al. (2012). Weft hair extensions causing a distinctive horseshoe pattern of traction alopecia. Journal of the American Academy of Dermatology, 67(6), e294-e295.
Aktas et al. (2016). Could Topical Minoxidil Cause Non-Arteritic Anterior Ischemic Optic Neuropathy?. Journal of clinical and diagnostic research: JCDR, 10(8), WD01: 1-2.
Avitzur, O. (2013). The dangers of hair extensions: The beauty trend can cause headaches, baldness, and allergic reactions. Consumer Reports. Retrieved on Aug. 7, 2017 from https://www.consumerreports.org/cro/2013/02/the-dangers-of-hair-extensions/index.htm.
Avram et al. (2014). Side-effects from follicular unit extraction in hair transplantation. Journal of cutaneous and aesthetic surgery, 7(3), 177-179.
Barrera, A. (2005). Reconstructive hair transplantation of the face and scalp. In Seminars in Plastic Surgery 19(2): pp. 159-166.
Barrese et al. (2016). Scanning electron microscopy of chronically implanted intracortical microelectrode arrays in non-human primates. Journal of neural engineering, 13(2), 026003: 1-44.
Bascom, J. (1983). Pilonidal disease: long-term results of follicle removal. Diseases of the colon & rectum, 26(12), 800-807.
Benedetto et al. (2005). Pilonidal sinus disease treated by depilation using an 800 nm diode laser and review of the literature. Dermatologic surgery, 31(5), 587-591.
Bernard, B. A. (2016). Advances in understanding hair growth. F1000Research, 5: 1-8.
Bernstein, R. (2009). Psychological Aspects of Balding. Bernstein Medical Center for Hair Restoration. Retrieved on Aug. 4, 2017 from https://www.bernsteinmedical.com/hair-loss/basics/psychology-of-balding/.
Biofibre (2015). Hair Implant Safety. Biofibre: High Technology Hair Implant System. Retrieved on Aug. 7, 2017 from http://www.biofibre.com/en/hair-implants/safety/.
Biofibre (2015). Results. Biofibre: High Technology Hair Implant System. Retrieved on Aug. 7, 2017 from http://www.biofibre.com/en/results/.
Bryers et al. (2012). Engineering biomaterials to integrate and heal: the biocompatibility paradigm shifts. Biotechnology and bioengineering, 109(8), 1898-1911.
Cash, T. F. (1992). The psychological effects of androgenetic alopecia in men. Journal of the American Academy of Dermatology, 26(6), 926-931.
Chavoin et al. (2016). Correction of congenital malformations by custom-made silicone implants: Contribution of computer-aided design. Experience of 611 cases. In Annales de chirurgie plastique et esthetique, vol. 61, No. 5, pp. 694-702.
Chellini et al. (2015). Generalized hypertrichosis induced by topical Minoxidil in an adult woman. International journal of trichology, 7(4), 182-183.
Cochrane Database of Systematic Reviews: Plain Language Summaries (2008). Treatments for alopecia areata. alopecia totalis, and alopecia universalis. Plain Language Summary of Delamere (2008). Interventions for alopecia areata. The Cochrane Library. Art. No. CD004413. p. 1.
Cochrane Database of Systematic Reviews: Plain Language Summaries (2016). Treatments for female pattern hair loss. Plain Language Summary of van Zuuren et al. (2016). Interventions for female pattern hair loss. Cochrane Database of Systematic Reviews 2016, Issue 5. Art. No. CD007628, p. 1-2.
Cotsarelis et al. (2001). Towards a molecular understanding of hair loss and its treatment. Trends in molecular medicine, 7(7), 293-301.
Duverger et al. (2014). To grow or not to grow: hair morphogenesis and human genetic hair disorders. Seminars in cell & developmental biology. vol. 25: pp. 22-33.
Erlich et al. (2003). Nasal dorsal augmentation with silicone implants. Facial plastic surgery, 19(04), 325-330.
Fanous et al. (2003). Estimating implant size in chin augmentation: A simplified approach. Canadian Journal of Plastic Surgery, 11(3), 161-165.
Farrell et al. (2014). Effects of pore size, implantation time, and nano-surface properties on rat skin ingrowth into percutaneous porous titanium implants. Journal of Biomedical Materials Research Part A, 102(5), 1305-1315.
Federal Drug Administration (2016). Sec. 895.101 Prosthetic Flair Fibers. CFR Title 21, vol. 8, Chapter 1, Subchapter H, Part 895, Subpart B. Retrieved on Aug. 4, 2017 from https://www.accessdata.fda.gov/scripts/cdrh/cfdocs/cfcfr/CFRSearch.cfm?fr=895.101.
Fleckman et al. (2008). Models for the histologic study of the skin interface with percutaneous biomaterials. Biomedical Materials, 3(3), 034006: 1-24.
Fleckman et al. (2012). Cutaneous and inflammatory response to long-term percutaneous implants of sphere-templated porous/solid poly (HEMA) and silicone in mice. Journal of Biomedical Materials Research Part A, 100(5), 1256-1268.
Fox et al. (2007). Traction folliculitis: an underreported entity. Cutis, 79(1), 26-30.
Gooding et al. (2004). The cadherin—catenin complex as a focal point of cell adhesion and signalling: new insights from three-dimensional structures. Bioessays, 26(5), 497-511.
Grice et al. (2011). The skin microbiome. Nature reviews. Microbiology, 9(4), 244-253.
Hanke et al. (1981). Hair implant complications. JAMA, 245(13), 1344-1345.

(56) References Cited

OTHER PUBLICATIONS

Hanke et al. (1981). Fiber implantation for pattern baldness. Am Acad Dermatol 4(3): 278-283.
Hartsock et al. (2008). Adherens and tight junctions: structure, function and connections to the actin cytoskeleton. Biochimica et Biophysica Acta (BBA)—Biomembranes, 1778(3), 660-669.
Hinderer, U. T. (1991). Nasal base, maxillary, and infraorbital implants—alloplastic. Clinics in plastic surgery, 18(1), 87-105.
Hirshburg et al. (2016). Adverse effects and safety of 5-alpha reductase inhibitors (finasteride, dutasteride): a systematic review. The Journal of clinical and aesthetic dermatology, 9(7), 56-62.
International Society of Hair Restoration Surgery (2003). Psychological effects of hair loss in women. Retrieved on Aug. 4, 2017 from http://www.ishrs.org/articles/hair-loss-effects.htm.
Jasterzbski et al. (2015). Pseudofolliculitis cutis: a vexing disorder of hair growth. British Journal of Dermatology, 172(4), 878-884.
Jones et al. (2013). Characterization of X-linked hypohidrotic ectodermal dysplasia (XL-HED) hair and sweat gland phenotypes using phototrichogram analysis and live confocal imaging. American Journal of Medical Genetics Part A, 161(7), 1585-1593.
Kaplan et al. (2012). A 5-year retrospective analysis of 5α—reductase inhibitors in men with benign prostatic hyperplasia: finasteride has comparable urinary symptom efficacy and prostate volume reduction, but less sexual side effects and breast complications than dutasteride. International journal of clinical practice, 66(11), 1052-1055.
Karaçal et al. (2012). Necrosis of the donor site after hair restoration with follicular unit extraction (FUE): a case report. Journal of Plastic, Reconstructive & Aesthetic Surgery, 65(4), e87-e89.
Karaman et al. (2006). Androgenetic alopecia: Does its presence change our perceptions?. International journal of dermatology, 45(5), 565-568.
Khanna et al. (2011). Pilonidal disease. Clinics in colon and rectal surgery, 24(01), 046-053.
Kong et al. (2012). Skin microbiome: looking back to move forward. Journal of Investigative Dermatology, 132(3), 933-939.
Konishi et al. (2012). Reshaping the eyebrow by follicular unit transplantation from excised eyebrow in extended infrabrow excision blepharoplasty. Clinical ophthalmology (Auckland, NZ), 6, 247-252.
Lei et al. (2016). Biofunctionalization of silicone rubber with microgroove-patterned surface and carbon-ion implantation to enhance biocompatibility and reduce capsule formation. International journal of nanomedicine, 11, 5563-5572.
Lepaw, M. I. (1979). Complications of implantation of synthetic fibers into scalps for "hair" replacement: experience with fourteen cases. The Journal of dermatologic surgery and oncology, 5(3), 201-204.
Lepaw, M. I. (1980). Therapy and histopathology of complications from synthetic fiber implants for hair replacement: A presentation of one hundred cases. Journal of the American Academy of Dermatology, 3(2), 195-204.
Mapes, D. (2008). The fallout of hair loss: Suffering in silence. Skin and beauty. NBC News. Retrieved on Aug. 4, 2017 from http://www.nbcnews.com/id/26895411/ns/health-skin_and_beauty/t/fallout-hair-loss-suffering-silence/#WaWCdMmYbF5.
MedlinePlus (2017). Hair loss. Health Topics. MedlinePlus. Retrieved on Aug. 4, 2017 from https://medlineplus.gov/hairloss.html.
MedlinePlus (2017). Hair loss. Medical Encyclopedia. MedlinePlus. Retrieved on Aug. 4, 2017 from https://medlineplus.gov/ency/article/003246.htm.
MedlinePlus (2017). Pilonidal sinus disease. Medical Encyclopedia. MedlinePlus. Retrieved on Aug. 4, 2017 from https://medlineplus.gov/ency/article/003253.htm.
Mirmirani et al. (2014). Traction Alopecia. Dermatologic clinics, 32(2), 153-161.
Moore et al. (2015). Molecular characterization of macrophage-biomaterial. Adv Exp Med Biol. 865: 109-122.
Motofei et al. (2017). Safety Profile of Finasteride: Distribution of Adverse Effects According to Structural and Informational Dichotomies of the Mind/Brain. Clinical Drug Investigation, 37(6), 511-517.
Murphy et al. (2010). The effect of mean pore size on cell attachment, proliferation and migration in collagen—glycosaminoglycan scaffolds for bone tissue engineering. Biomaterials, 31(3), 461-466.
Mysore, V. (2010). Controversy: Synthetic hairs and their role in hair restoration?. International journal of trichology, 2(1), 42-44.
Nayyer et al. (2016). A biodesigned nanocomposite biomaterial for auricular cartilage reconstruction. Advanced healthcare materials, 5(10), 1203-1212.
NIDO Ltd (2006). What's new. Retrieved on Aug. 4, 2017 from http://www.nidohq.co.jp/nido_english/what/what.html.
Niechajev, I. (2012). Facial reconstruction using porous high-density polyethylene (medpor): long-term results. Aesthetic plastic surgery, 36(4), 917-927.
Oh et al. (2016). A guide to studying human hair follicle cycling in vivo. Journal of Investigative Dermatology, 136(1), 34-44.
Otberg et al. (2004). Variations of hair follicle size and distribution in different body sites. Journal of Investigative Dermatology, 122(1), 14-19.
Pae et al. (1975). Design and evaluation of a percutaneous transthoracic cannula. Transactions—American Society for Artificial Internal Organs, 22, 135-148.
Palmieri et al. (2000). Evaluation of polyamide synthetic hair. A long-term clinical study. Panminerva medica, 42(1), 49-53.
Patel et al. (2016). Solid implants in facial plastic surgery: potential complications and how to prevent them. Facial Plastic Surgery, 32(05), 520-531.
Peluso et al. (1992). Cutaneous complications of artificial hair implantation: a pathological study. Dermatology, 184(2), 129-132.
Perry et al. (2002). Defining pseudofolliculitis barbae in 2001: a review of the literature and current trends. Journal of the American Academy of Dermatology, 46(2), S113-S119.
Poswal et al. (2011). When FUE goes wrong!. Indian journal of dermatology, 56(5), 517-519.
Raposio et al. (2015). Scalp surgery: quantitative analysis of follicular unit growth. Plastic and Reconstructive Surgery Global Open, 3(10): 1-4.
Rose, P. T. (2015). Hair restoration surgery: challenges and solutions. Clinical, cosmetic and investigational dermatology, 8, 361-370.
Rutala et al. (2008). Guideline for disinfection and sterilization in healthcare facilities, 2008. Department of Health and Human Services. Centers for Disease Control and Prevention. pp. 1-161.
Santiago et al. (2007). Artificial hair fiber restoration in the treatment of scalp scars. Dermatologic surgery, 33(1), 35-44.
Scharschmidt et al. (2013). What lives on our skin: ecology, genomics and therapeutic opportunities of the skin microbiome. Drug Discovery Today: Disease Mechanisms, 10(3), e83-e89.
Schneeberger et al. (2004). The tight junction: a multifunctional complex. American Journal of Physiology—Cell Physiology, 286(6), C1213-C1228.
Sengul et al. (2009). Axillary pilonidal sinus: A case report. North American journal of medical sciences, 1(6), 316-318.
Serdev et al. (2015). Polyamide hair implant (biofibre®): evaluation of efficacy and safety in a group of 133 patients. Journal of Biological Regulators & Homeostatic Agents, 29(1), 107-113.
Shao et al. (2014). Follicular unit transplantation for the treatment of secondary cicatricial alopecia. Plastic Surgery, 22(4), 249-253.
Shiell et al. (1990). Problems associated with synthetic fibre implants for hair replacement ("NIDO" process). The Medical journal of Australia, 152(10), 560.
Sinclair et al. (2015). Androgenetic alopecia: new insights into the pathogenesis and mechanism of hair loss. F1000Research, 4(F1000 Faculty Rev): 585: 1-9.
Sluysmans et al. (2017). The role of apical cell-cell junctions and associated cytoskeleton in mechanotransduction. Biology of the Cell (109): 139-161.
Tang, V. W. (2006). Proteomic and bioinformatic analysis of epithelial tight junction reveals an unexpected cluster of synaptic molecules. Biology direct, 1(1), 37: 1-30.

(56) References Cited

OTHER PUBLICATIONS

Tchernev et al. (2016). Biofibre hair implant: what is new, what is true?. Journal of biological regulators and homeostatic agents, 30(2 Suppl 2), 49-56.
Figure 1 of Teumer et al. (May 2005). Follicular cell implantation: an emerging cell therapy for hair loss. In Seminars in Plastic Surgery (vol. 19, No. 02, pp. 193-200).
Thiedke, C. C. (2003). Alopecia in women. American family physician, 67(5), 1007-1014.
Toyoshima et al. (2012). Fully functional hair follicle regeneration through the rearrangement of stem cells and their niches. Nature communications, 3, 784: 1-12.
Uebel, C. O. (2005). The punctiform technique in hair transplantation. Seminars in Plastic Surgery, vol. 19, No. 02, pp. 109-127.
Underwood et al. (2011). Quantifying the effect of pore size and surface treatment on epidermal incorporation into percutaneously implanted sphere-templated porous biomaterials in mice. Journal of Biomedical Materials Research Part A, 98(4), 499-508.
Unknown. (2017). Image of hair root. Trends in Molecular Medicine. Retrieved on Aug. 24, 2017 from http://www.cell.com/cms/attachment/553998/3951952/gr1.jpg.
Unknown. (2015). Image of Hair transplant surgery scars in donor area with follicular unit extraction technique. Retrieved on Aug. 25, 2017 from http://ae154zl15g.previewdomain.jp/wp-content/uploads/2015/11/003_BK2.jpg.
Unknown. (2013). Image of Galea aponeurotica seen though scalp incision. Retrieved on Aug. 24, 2017 from http://www.the-dermatologist.com/sites/default/files/issues/Screen%20Shot%202013-08-20%20at%209.00.40%20AM.png.
Unknown (2015). Galea aponeurotica diagram. Retrieved on Aug. 25, 2017 from http://www.learnneurosurgery.com/uploads/1/6/6/8/16689668/1813531.jpg?702.
Unknown (2015). Galea aponeurotica diagram with head in view. Retrieved on Aug. 24, 2017 from http://www.buism.com/hairloss_files/image001.jpg.
Vanhoestenberghe et al. (2013). Corrosion of silicon integrated circuits and lifetime predictions in implantable electronic devices. Journal of neural engineering, 10(3), 031002: 1-13.
Wai, S. (2014). What is hair implant?. Skin health: the creation of beauty is art. Retrieved on Aug. 24, 2017 from http://skinhealthsubang.blogspot.com/2014/08/what-is-hair-implant.html.
Abstract of Wan et al. (2017). Solvent Bonding for Fabrication of PMMA and COP Microfluidic Devices. JoVE (Journal of Visualized Experiments), (119), e55175-e55175.
Wikipedia (2017). Injection molding of liquid silicone rubber. Wikipedia, the free encyclopedia. Retrieved on Aug. 24, 2017 from https://en.wikipedia.org/w/index.php?title=Injection_molding_of_liquid_silicone_rubber&oldid=787919147.
Wikipedia (2017). Injection moulding. Wikipedia, the free encyclopedia. Retrieved on Aug. 7, 2017 from https://en.wikipedia.org/w/index.php?title=Injection_moulding&oldid=794136890.
Wikipedia (2017). Silicone rubber. Wikipedia, the free encyclopedia. Retrieved on Aug. 7, 2017 from https://en.wikipedia.org/w/index.php?title=Silicone_rubber&oldid=788264103.
Wilt et al. (2008). 5-alpha-reductase inhibitors for prostate cancer prevention (review). Cochrane Database of Systematic Reviews, Issue 2: 1-61.
International Search Report for related PCT Application No. PCT/US2019/038950 dated Sep. 13, 2019.

* cited by examiner

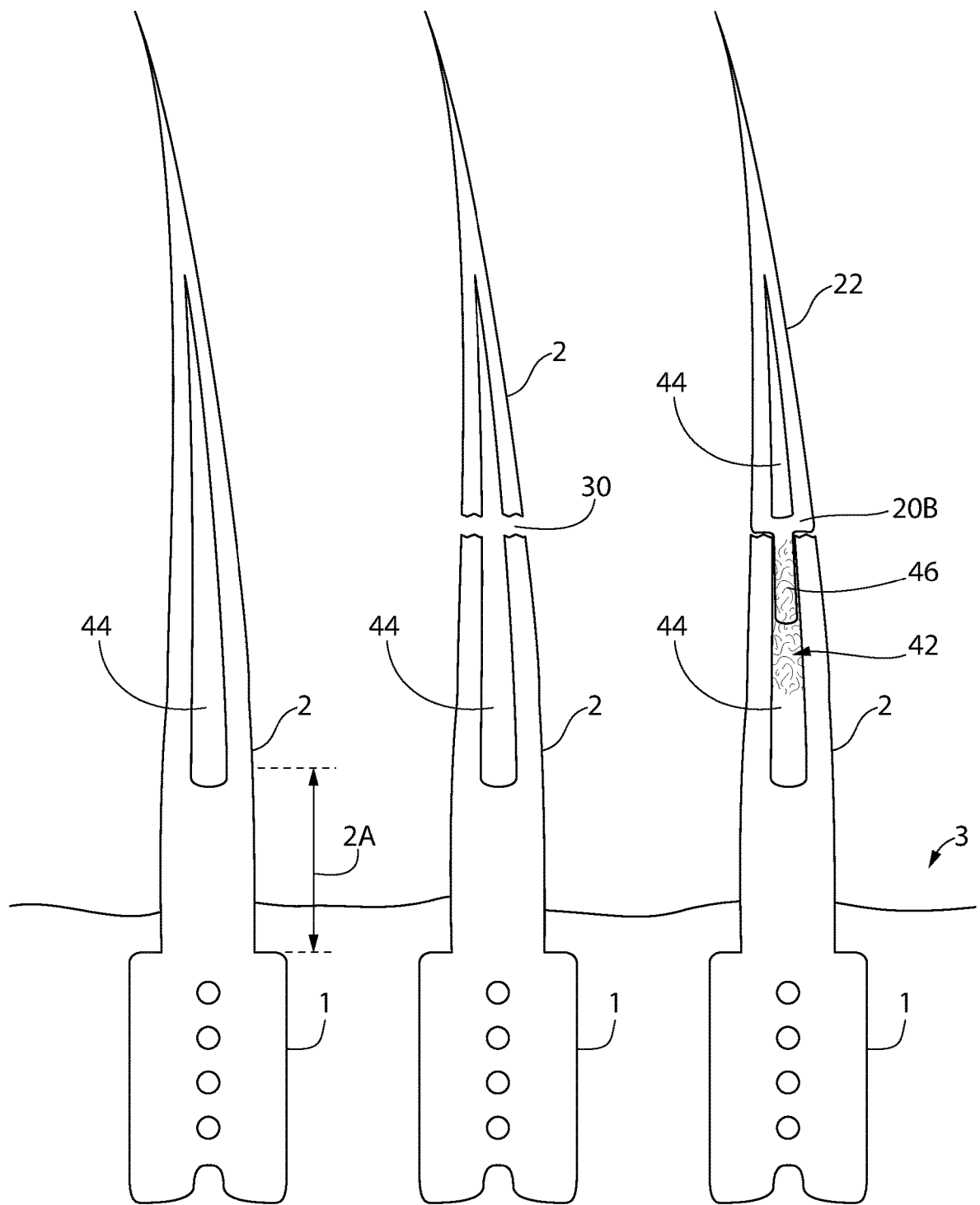

EXTENSION APPARATUS FOR ARTIFICIAL HAIR IMPLANTS

CROSS-REFERENCE TO RELATED APPLICATIONS

This bypass continuation-in-part application claims the benefit under 35 U.S.C. § 120 of international application PCT/US2018/044298 filed on Jul. 30, 2018 which in turn claims the claim benefit under 35 U.S.C. § 120 of both U.S. application Ser. No. 15/665,369, filed on Jul. 31, 2017 (now U.S. Pat. No. 9,993,334) and U.S. application Ser. No. 15/718,637 filed on Sep. 28, 2017 (now U.S. Pat. No. 10,105,212), all of which are entitled HAIR IMPLANTS COMPRISING ENHANCED ANCHORING AND MEDICAL SAFETY FEATURES and all of whose entire disclosures are incorporated by reference herein. U.S. application Ser. No. 15/718,637 (now U.S. Pat. No. 10,105,212) is also a continuation-in-part application and claims the benefit under 35 U.S.C. § 120 of U.S. application Ser. No. 15/665,369 (now U.S. Pat. No. 9,993,334).

BACKGROUND OF THE INVENTION

1. Field of Invention

This invention relates to the field of hair replacement and more particularly to artificial hair implantation and the extension and repair of implanted hairs.

2. Description of Related Art

For millennia men and women have been concerned, ridiculed, and even suicidal regarding hair loss and the physical and cosmetic impact it makes upon ones' appearance, especially the loss of scalp or facial hair (2-6). Causes of hair loss are numerous including genetic disorders, genetic inheritance, stress from illness, fever, or physical activity, chemotherapy, pulling on hair, curling irons, chemical processing of hair for shaping or coloring etc., aging, poor diet, thyroid disease, ringworm, and many other skin and non-skin diseases too lengthy to list here (1,7,8,13,14, 17).

While artificial hair has been used to ameliorate the appearance of hair loss, hair pieces or hair implants often do not look or feel natural, as they repeatedly fail to possess the correct color, texture, volume, or density patterns to match existing natural hair growth. Additionally, styling artificial hair is challenging, as hair strands become permanently shortened through daily breakage or cutting the hair.

Hair extensions have been utilized to add length and volume to existing natural hair. Removable hair pieces that can be attached via clips, combs, snaps, or interlocking strips can give the appearance of length, but often are not customized to fit the appearance of the natural hair (18). Moreover, they only provide a temporary solution for shortened hair or hair loss. For a more permanent option, many hair extensions are held together by a vinyl strip that attaches near the roots of existing hair with an adhesive (19). Additionally, other hair extensions are attached to existing hair by looping a natural hair lock through a ring structure to which an extension is attached (20). The ring structure then slides to the base of the natural hair and is crimped to fasten the extension in place. However, this risks the possibility of extensions falling out through daily use, as the rings create obstacles during the hair grooming process. Other extensions require that natural hair be tied or weaved together with the artificial extensions, generating possibilities of damage to existing hair. (21). Even for those with a natural base of hair, these attachment methods can prove to be uncomfortable for the wearer, limiting hair extension options for those looking for semi-permanent hair length with a natural feel.

Despite the multitude of hair extensions on the market, most extensions require an adequate natural hair base to which they are able to attach. For those that do not wish to wear wigs and have hair loss to the degree where traditional extensions cannot be discretely and securely fastened, some have looked to hair implants as a solution. These aforementioned implant systems are preferred, but do not limit the scope of the invention.

However, even successfully placed hair implants with minimal or no side effects have limitations, as they contain artificial hair that is permanently shortened once breakage occurs or the strands are cut. Hair implants often do not support the application of traditional hair extensions, as these extensions not only place strain on the hair anchor, but also fail to securely attach. Once breakage or shortening of the artificial hair occurs, it is difficult to maintain desired volume, length, and density patterns necessary to achieve natural looking hair. Thus, there remains a need for a means of attaching extensions or ancillary hairs to the implanted hair, creating a natural, voluminous, and lengthy appearance without placing excessive strain on the implant anchor.

Incorporated by reference herein in their entireties are U.S. Pat. No. 9,993,334 (Loria), U.S. Pat. No. 10,105,212 (Loria) and PCT/US2018/044298 (Lorstan Pharmaceutical LLC) and U.S. Pat. No. 5,061,284 (Laghi).

SUMMARY OF THE INVENTION

An extension apparatus for an artificial implanted hair element in a patient's epidermis is disclosed. The artificial implanted hair element projects beyond the epidermis and has a distal end. The extension apparatus comprises: a cylindrical structure having a first end with a first cavity therein and a second end with a second cavity therein; and wherein the first cavity is configured to receive the distal end therein and the second cavity is configured to receive at least one hair extension element therein.

Another extension apparatus for an artificial implanted hair element in a patient's epidermis is disclosed. The artificial implanted hair element projects beyond the epidermis and comprises a hollow interior and wherein the artificial implanted hair element has a distal end. The extension apparatus comprises: a hair extension having a hair extension element forming a first portion of the hair extension and a projection forming a second portion, opposite the first portion, for being received inside the hollow interior of the artificial implanted hair element; and wherein the hair extension element comprises a hollow portion.

A further extension apparatus for an artificial implanted hair element in a patient's epidermis is disclosed. The artificial implanted hair element projects beyond the epidermis and wherein the artificial implanted hair element has a distal end. The extension apparatus comprises: a hair extension comprising a core having a hair extension element projecting from one side of the core and a single cavity located on a second side, opposite the one side, of said core, and wherein the single cavity is configured for receiving the distal end of the artificial implanted hair element therein.

An even further extension apparatus for an artificial implanted hair element in a patient's epidermis is disclosed. The artificial implanted hair element projects beyond the epidermis and has a distal end. The apparatus comprises: a hair extension element having distal portion and a proximal portion, wherein the distal portion comprises ancillary hair elements and wherein the ancillary elements comprise bud structures wherein the bud structures provide points of attachment for further hair extensions if desired; and wherein the proximal portion of the hair extension is configured for being adhesively connected to the distal end of the artificial implanted hair element.

A hair implant suitable for subcutaneous implantation within a patient is disclosed. The hair implant comprises: an anchor body having a plurality of apertures therethrough and wherein the anchor body is configured for subcutaneous implantation, the anchor body comprising at least two artificial hair elements that protrude from a distal end of the anchor body and wherein the at least two artificial hair elements are configured for projecting out of the epidermis of the patient; at least one of the two artificial hair elements comprising ancillary hair elements and wherein the ancillary hair elements comprise bud structures thereon wherein the bud structures provide points of attachment for further hair extensions if desired; and wherein the other one of the at least two artificial hair elements comprises an extension apparatus (e.g., an extension apparatus having a cylindrical structure, or a combined hair extension element and an opposed projection, or a combined hair extension element on one end and a single cavity on the opposite end, etc.) for attaching a hair extension to a distal end of the other one of said at least two artificial hair elements.

In certain embodiments, the hair bud structure is solid.

In certain embodiments, the hair bud structure is hollow.

In certain embodiments, the hair extension element comprises ancillary hairs that are molded to the shaft of the primary hair.

In certain embodiments, the hair extension element comprises at least one hair bud structure.

In certain embodiments, the hair extension element is a synthetic hair comprising polymer filaments selected from the group consisting of polypropylene, polyvinyl chloride, polyamide, polyethylene, polyacrylonitrile, polyvinylidene chloride, polyurethane, polyester, and copolymers thereof.

In certain embodiments, a method of securing an extension apparatus to an artificial implant hair, comprising: (a) attaching the artificial implant hair to an extension apparatus, and (b) utilizing an attachment technique independently selected from the group of: friction, heat, adhesive, or chemical reaction.

In certain embodiments, attaching the artificial implant hair to the attachment apparatus further comprises inserting the distal end of the implant hair into the proximal cavity of the extension apparatus.

In certain embodiments, attaching the artificial implant hair to the attachment apparatus further comprises inserting the proximal end of at least one extension element into the distal cavity of the extension apparatus.

In certain embodiments attaching the artificial implant hair to the attachment apparatus further comprises: (a) utilizing an implant hair with a hollow core, and (b) inserting the proximal protrusion of the attachment apparatus element into the hollow core of the implant hair.

In certain embodiments, attaching the artificial implant hair to the attachment apparatus comprises: (a) utilizing a solid hair bud structure; and (b) inserting the hair bud structure into the proximal cavity of the extension apparatus.

In certain embodiments, attaching the artificial implant hair to the extension apparatus comprises: (a) utilizing a hollow hair bud structure, and (b) inserting the proximal protrusion of the extension apparatus into the hollow hair bud structure.

A method for forming a hair extension on an artificial implanted hair element in a patient's epidermis is disclosed. The artificial implanted hair element projects beyond the epidermis and has a distal end. The method comprises: forming a cylindrical structure having a first end with a first cavity therein and a second end with a second cavity therein; positioning a portion of at least one hair extension element into the first cavity therein and securing the portion therein; and positioning the distal end of the artificial implanted hair into the second cavity and securing (e.g., using friction, heat, adhesive or other chemical means, etc.) the distal end therein.

A method for forming a hair extension on an artificial implanted hair element in a patient's epidermis is disclosed. The artificial implanted hair element projects beyond the epidermis and comprises a hollow interior. The artificial implanted hair element has a distal end. The method comprises: molding a hair extension element on a first end of a hair extension; forming a projection at a second end, opposite the first end; inserting the projection inside the hollow interior of the artificial implanted hair element; and securing (e.g., using friction, heat, adhesive or other chemical means, etc.) the projection inside the hollow interior of the artificial implanted hair element.

A method for forming a hair extension on an artificial implanted hair element in a patient's epidermis is disclosed. The artificial implanted hair element projects beyond the epidermis and has a distal end. The method comprises: molding a hair extension on first end of a hair extension core; forming a single cavity on a second end, opposite the first end, of the core; inserting the distal end of the artificial implanted hair element within the single cavity; and securing (e.g., using friction, heat, adhesive or other chemical means, etc.) the distal end inside the single cavity.

A method for forming a hair extension on an artificial implanted hair element in a patient's epidermis is disclosed. The artificial implanted hair element projects beyond the epidermis and has a distal end. The method comprises: molding a hair extension element having a distal portion and a proximal portion and forming ancillary hair elements, having bud structures thereon, on the distal portion; and adhesively connecting the proximal portion of the hair extension to the distal end of the artificial implanted hair element.

A method for forming a hair implant suitable for subcutaneous implantation within a patient is disclosed. The method comprises: forming an anchor body having a plurality of apertures therethrough and wherein the anchor body is configured for subcutaneous implantation; forming at least two artificial hair elements that protrude from a distal end of the anchor body and wherein at least one of the two artificial hair elements is formed with ancillary hair elements having bud structures thereon, the bud structures providing points of attachment for further hair extensions; securing (e.g., using friction, heat, adhesive or other chemical means, etc.) an extension apparatus, comprising the hair extension, to a distal end of the other one of the at least two artificial hair elements to join the hair extension on the other one of the at least two artificial hair elements.

BRIEF DESCRIPTION OF SEVERAL VIEWS OF THE DRAWINGS

The invention will be described in conjunction with the following drawings in which like reference numerals designate like elements and wherein:

FIG. 2B shows an enlarged side view of a hair implant comprising a hair anchor and artificial hair element with a hollow inner core;

FIG. 2C depicts the artificial implant hair of FIG. 2B having suffered a breakage;

FIG. 2D depicts the broken artificial implant hair of FIG. 2C being repaired using the second attachment apparatus of FIG. 2A;

DETAILED DESCRIPTION OF PREFERRED EMBODIMENTS OF THE INVENTION

Figure 1A:
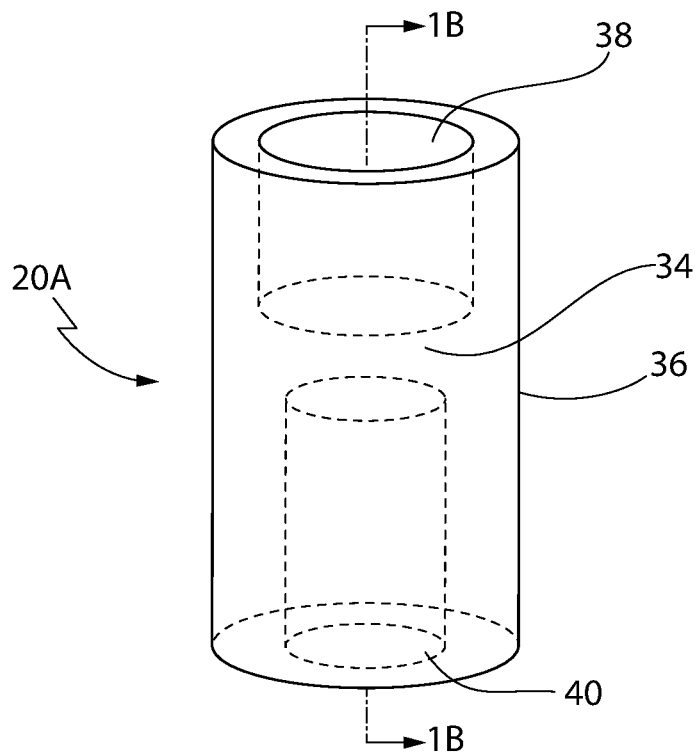
FIG. 1A is an enlarged isometric view of a first hair extension attachment apparatus of the invention.

The goal of adding artificial hair elements to the body is to achieve a natural appearance with minimal to no side effects. Observing the natural form of existing living hair follicles and their anatomy has provided valuable information regarding desirable structural and functional elements of artificial hair implant extension materials, design, and attachment technique.

Natural hair visibly appears exiting from the skin from the deeper dermal layer. This is a very important observation (9,10). If one examines traditional hair weaves, hair extensions, or similar hair systems, the hair exits from above the skin and often looks unnatural when it does not match the natural hair color or hair density patterns that are found with natural hair growth on the sides and back of the scalp. Upon close inspection of these hair systems, it is possible to see the artificial substrate to which the hair is anchored. In addition, the hair system requires some type of mechanism for anchoring the substrate to the skin itself, such as tape, glue, or some type of clip. This type of system is like wearing a thick wooly hat which can be uncomfortable at times regarding heat, sweating, and irritation.

Natural anatomic hair density and patterns vary according to a person's age and sex. Extending the length of implanted hairs with an extension system serves as a method of achieving a lengthier and denser appearance even when there are few naturally grown hairs to which the extensions may adhere. Ideally, achieving the appropriate hair density results may be aided by utilizing a sleek and narrow implant design which allows close placement or approximation between each hair implant. The hair implant design preferably mimics the general size and shape of the natural hair follicle (11,12). This issue of achieving high hair densities becomes critical for women and young men because, in a large majority of times, they have very full and dense hair patterns showing no signs of hair loss, hair recess patterns, or any balding patterns whatsoever. Any type of hair restoration that yields a low-density look will result in a suboptimal look for such patients, which results in disappointment and low self-esteem.

Traditional use of artificial hair, such as hair pieces, weaves, wigs, etc., can achieve the hair density and pattern, but these systems are just too unnatural looking and are very uncomfortable generating heat, sweat, and, in addition, skin irritation, inflammation and traction alopecia resulting in further natural hair loss (13-16).

There are about 100,000 hairs on the human scalp, and about 5 million on the human body. There are about 120 square inches of hair bearing skin on the scalp. Each square inch, or 6.4 square centimeters, comprises 833 hairs, or about 130 hairs per square centimeter.

Hair loss is not perceived or observed until about 50% is lost. The ultimate goal in hair restoration is to achieve the appearance of a full head of hair, which can be achieved by providing only 50% of the normal quantity of hair per unit area. The invention can provide the appearance of a full head of hair or something less for those whose hair restoration goals are more modest.

The invention preferably enables adding hair extensions to implanted hairs to add volume, length, and/or repair breakage. The extra density will maintain the appearance of a full head of hair for a greater length of time.

Upon examining the scalp, it will be observed that most hair follicles naturally group close together in clusters, and typically are not isolated as single hair follicles. These natural groupings are termed "follicular units" or FUs. This aspect of natural anatomy has been taken into consideration in the design and manufacturing of the artificial hair implant extensions.

Creating an extension system allowing for ancillary hairs to attach to hair extension strands not only adds length to shortened hair and repairs breakage, but also adds volume by resembling the clusters of hair naturally found in FUs. This system even allows for more hair to be added over time through the use of hair bud structures, counteracting progressive hair loss.

Thus, there are several features in the natural anatomic design that can be emulated in the artificial design to meet the patient's goals of achieving a full or near full complement of naturally feeling and looking hair. Artificial implant hair extension apparatuses of the invention preferably provide one or more of the following features: (1) the implant hair and the extension element meeting in a natural, continuous-looking fashion, (2) natural hair density and pattern, and (3) appropriate anchoring of the hair extension to the implant hair to prevent the extension strands from falling out.

Hair Implantation: Structure, Function, and New Innovative Considerations

Natural Look

Obtaining the natural look of hair length and density can be accomplished by emulating the natural hair fiber. The hair strand(s) within the extension apparatus can be tailored in color, shape, length, etc., to the anatomic location and cosmetic desires and needs of the patient. For example, hair implant extensions can be custom designed to be long, short, straight, curly, black, or blonde, etc. Hair implant extensions can also be customized for the eyebrows, pubic, and other areas of the body. See, e.g., Otberg et al. (58).

Materials suitable for the hair extension strand component of the inventive extension apparatus include but are not limited to human hair, animal hair and synthetic polymers. Non-limiting examples of polymers suitable for synthetic hair include one or more of polypropylene, polyvinyl chloride, polyamide, polyethylene, polyacrylonitrile, polyvinylidene chloride, polyurethane and polyester.

Hair suitable for use in the invention can be straight, tightly curled or loosely curled. Suitable hair can be colored, partially colored or uncolored. The length of the hair fibers is not particularly limited, but suitable hair fibers are preferably at least 5 cm or at least 10 cm or at least 15 cm in length for ease of styling after application. Hair materials suitable for use in the invention preferably have a diameter similar to naturally occurring hair, for example, ranging from 0.02 to 0.2 mm. The cross-sectional shape of the hair is preferably elliptical or round, like naturally occurring hair.

Suitable hair for application of hair extensions includes solid hair, hair with a hollow internal hair chamber, hair with ancillary hairs stemming from the primary hair strand, and hair with budding structures that allow direct attachment of hair extension strands. Said hair may be of various textures and colors. Applied hair extensions may similarly be solid, possess a hollow internal hair chamber, possess a proximal protrusion, have ornamentation, have ancillary hairs, or feature hair budding structures. The hair extensions may also comprise various hair textures and colors.

Materials suitable for use if the attachment apparatus component of the invention include metals, plastics, silicone, rubber, and polymers of polypropylene, polyvinyl chloride, polyamide, polyethylene, polyacrylonitrile, polyvinylidene chloride, polyurethane and polyester.

Implant hair extensions may also be suitably attached through methods comprising adhesive, heat, chemical means, or an attachment apparatus that attaches the hair extension to the implant hair element via friction, heat, adhesive, or other chemical means.

Design

Introduction

The design used for the hair implant extension apparatuses of the invention involves hair extension elements of a certain length, texture, internal structure, external structure, and attachment mechanisms to optimize certain objectives such as providing secure attachment, natural and appropriate hair density and pattern placement, and structural integrity to prevent breakage.

Natural Look of Lengthened Hair

One key design factor for making hair implant extensions look as natural as possible is adding the extension apparatus to the end of an existing implant hair element, giving the appearance of a continuous strand of hair exiting the scalp. Natural hair exiting the scalp (with all of its natural anatomic features) is the ultimate goal to parallel.

The natural hair exiting the epidermis has certain anatomic features such the distal end of the hair implant extension having a tubular shape and minimal diameter. With an appropriate distal to proximal widening slope, the hair implant extension will allow internal sloping to be the same or similar to natural hair. Additionally, designing a wide array of colors, textures, lengths, and densities of extensions will allow the extension strand to match the appearance of the implanted strand, giving a cohesive look.

Hair Density and Hair Pattern

Hair density and patterns vary among men and women, among the young and old, among race and religions. Natural looking hair, whether the implants are sparsely or closely placed, can achieve the desired hair density and pattern goals for each patient. The high density or "very thick look", for the young and women, can be achieved by utilizing hair extension elements that have the ability to add ancillary hair elements, resulting in a dense natural hair pattern look. Conversely, a less dense extension can be utilized for elderly men, as desired.

Anchoring of the Hair Implant Extension

Design, involving the attachment apparatus will be the most significant aspects regarding hair implant extension anchoring. The attachment apparatus utilized will depend on the internal and external features of the implanted hair to which it will attach.

The internal structure of the implant hair to which the apparatus will attach may be solid or have a hollow core. Implant hair elements with hollow internal hair chambers or cores may be augmented with an extension containing an embodiment of the second attachment apparatus comprising a proximal protrusion to fit within the hollow chamber. This method is particularly effective to achieve a seamless connection between the implant hair and the extension strand. Solid hair elements may be augmented with an extension by being inserted into a further embodiment of an attachment apparatus such as the first or third attachment apparatuses that remain on the outside of the hairs.

The internal structure of the attachment apparatus may vary according to the embodiment. The first attachment apparatus comprises a solid cylindrical structure into which a first cavity on one end of the structure is formed while a second cavity is formed in the second opposite end of the structure. The implant hair inserts into one of the cavities, while the extension element(s) inserts into the other cavity. The third attachment apparatus also comprises a solid structure into which a single cavity is formed on one end of the structure. On the other end of the solid structure, opposite the single cavity, a hair extension element is molded to the attachment structure itself and may be a single hair, multiple hairs, or possess hair buds or ancillary hairs stemming off of primary hairs. The second attachment apparatus, however, comprises no cavities and instead possesses a protrusion that may be inserted into a hollow implant hair, hollow hair bud, or hollow extension strand. The fourth attachment apparatus also possesses this protrusion-like structure, but due to its ornamental nature, it can be modified to have the attachment mechanism of the first, second, or third attachment apparatuses used therewith.

The external structure of the hair extension element of the apparatus may contain ancillary hairs or hair bud structures. Ancillary hairs may be permanently attached to the primary hair of the extension. Hair bud structures may also emerge from the primary hair and serve as points of attachment for ancillary hairs. These structures may be solid or hollow protrusions and can allow for extra hair density and volume as well as for additional adding/subtracting of density and volume over time. For solid hair buds, an extension apparatus embodiment with an external attachment system, such as the first or third attachment apparatuses is preferable to add length to the primary hair. For hollow hair buds, an extension apparatus embodiment with an internal attachment system, such as the second or fourth attachment apparatuses is preferred, as the protrusion on the attachment apparatuses may insert into the hollow bud.

While the extension strands comprising the ancillary hair and hair bud structures are preferably attached with an apparatus, they may also be attached directly to the implant hair itself via adhesive, heat, or other chemical means.

Hair Implant Extension Features

There are two main concerns when making hair extensions—unnatural appearance and falling out.

Traditional artificial hair extensions may have an unnatural appearance, as the extension layer may sharply contrast with the overlying natural hair or the area of adhesion is visible. This problem can be alleviated with an extension that continues the existing strand of implanted hair, resulting in a lengthened, seamless look.

The following discussion of the present invention involves the use a hair implant anchor 1 implanted under the epidermis 3 of the patient and having an artificial hair element(s) 2, secured inside the implant anchor 1, and protruding from the epidermis 3. Although the structure of the hair implant 1 forms no limitation on the hair extensions and attachment devices discussed below, by way of example only, the hair implant anchor 1 may comprise those discussed in U.S. Pat. No. 9,993,334 (Loria), U.S. Pat. No. 10,105,212 (Loria) and PCT/US2018/044298, all of which are owned by the same Assignee as the present application, namely, Lorstan Pharmaceutical, LLC of Doral, Fla. and all of whose entire disclosures are incorporated by reference herein. These exemplary hair implants 1 (shown throughout the figures) comprise anchor bodies with a plurality of apertures or tunnels which are configured to receive and retain collagen ligatures (not shown) that are capable of anchoring the anchor body in the subcutaneous layer of the patient. It should be further noted that a trunk portion 2A of the implant hair 2 comprises a thicker zone diameter (e.g., 5-30 mm) than the remaining upper portion of the implant hair 2.

FIG. 1A shows an isometric view of a first attachment apparatus 20A of the invention. The first attachment apparatus 20A possesses a cylindrical outer shape with a distal cavity 38 and a proximal cavity 40 into which hair elements may be inserted.

Figure 1B:
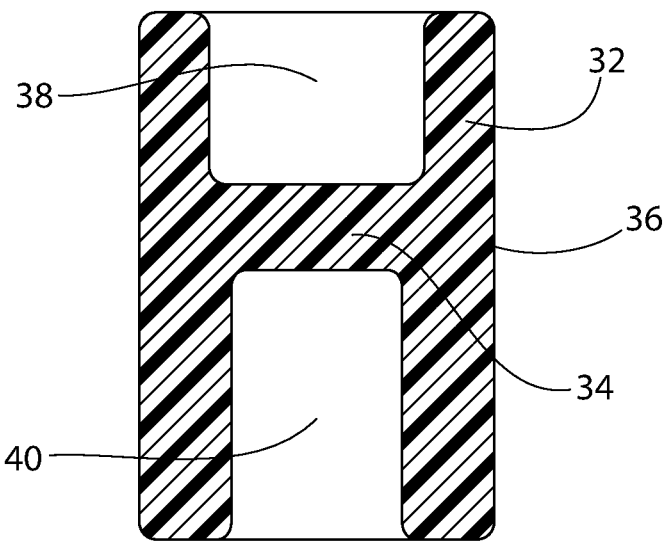
FIG. 1B is a cross-sectional view of the first attachment apparatus of FIG. 1A taken along line 1B-1B of FIG. 1A.

FIG. 1B shows a cross-sectional view of the first attachment apparatus 20A taken along line 1B-1B of FIG. 1A. The core of the apparatus 20A comprises a cylinder with the distal cavity 38 and the proximal cavity 40 formed therein, thereby resulting in an "H-shaped" configuration in cross-section (FIG. 1B). Thus, the core comprises a cylindrical sidewall 32 having an internal solid horizontal component 34 at a substantially central location 36.

Figures 1C, 1D, 1E:
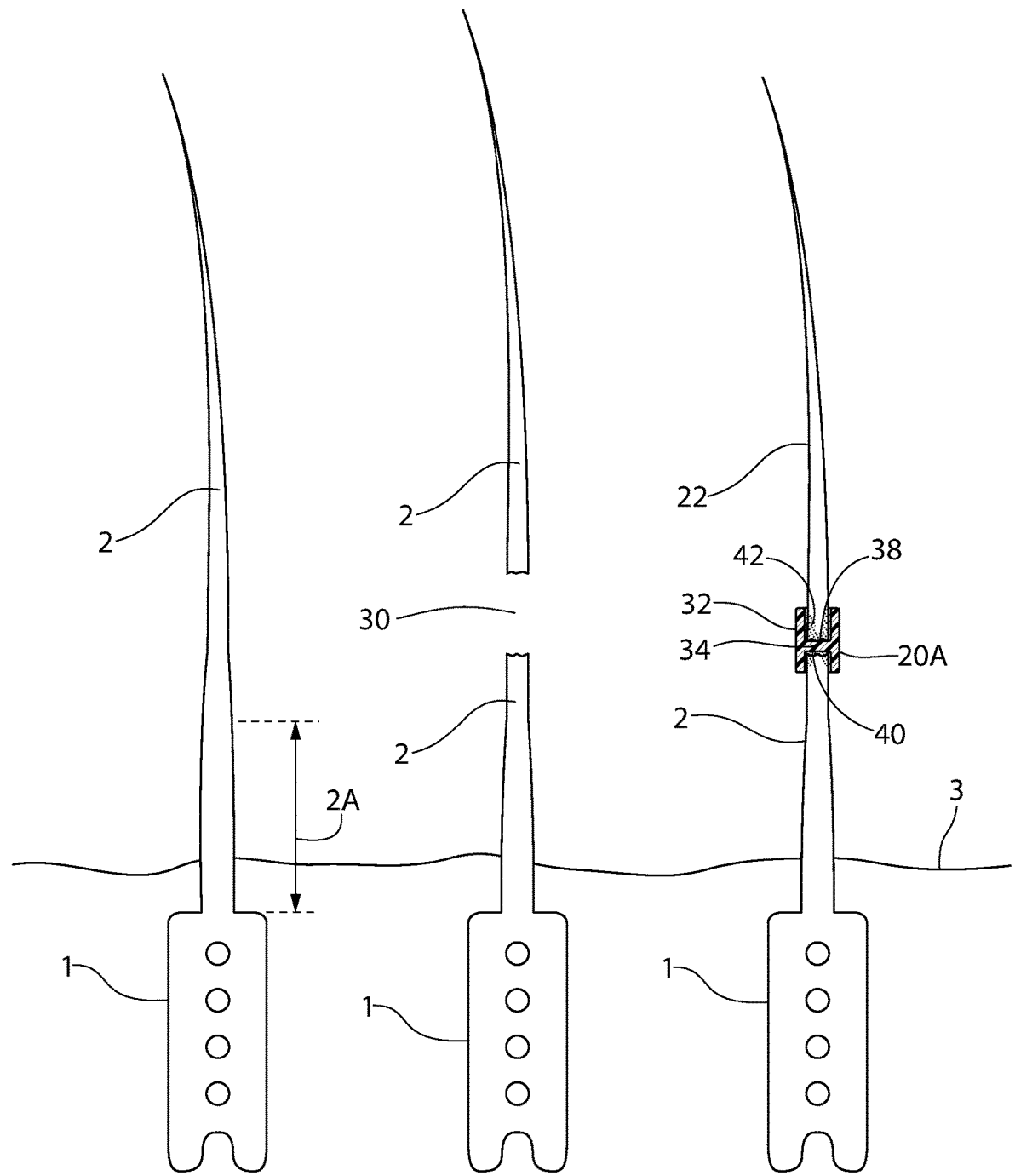
FIG. 1C shows an enlarged side view of a hair implant comprising a hair anchor and an artificial implant hair.
FIG. 1D depicts the artificial implant hair of FIG. 1C having suffered a breakage.
FIG. 1E depicts the broken artificial implant hair of FIG. 1D being repaired using the first attachment apparatus of FIG. 1A, shown in cross-section.

FIG. 1C shows a cross-sectional view of a hair implant comprising a hair anchor 1 and implant hair 2, wherein the implant is anchored within the epidermis 3.

FIG. 1D shows a cross-sectional view of the same implant of FIG. 1C, but wherein the implant hair 2 has been subjected to a breakage 30, resulting in a loose piece of the implant hair 2.

FIG. 1E shows a cross sectional view of the correction of the breakage in FIG. 1D using the first attachment apparatus 20A. In particular, the two formed cavities allow for insertion of the implant hair 2 into the proximal cavity 40 and the implant extension 22 into the distal cavity 38. The vertical sides 32 are in contact with the sides of the implanted hair 2 and the extension 22, providing stability. The implant hair 2 and extension 22 may be secured within the apparatus 20A with adhesive 42. Additional embodiments of the apparatus may allow for the securing of hair strands within the apparatus through heating, chemical reaction, or friction.

Figure 2A:
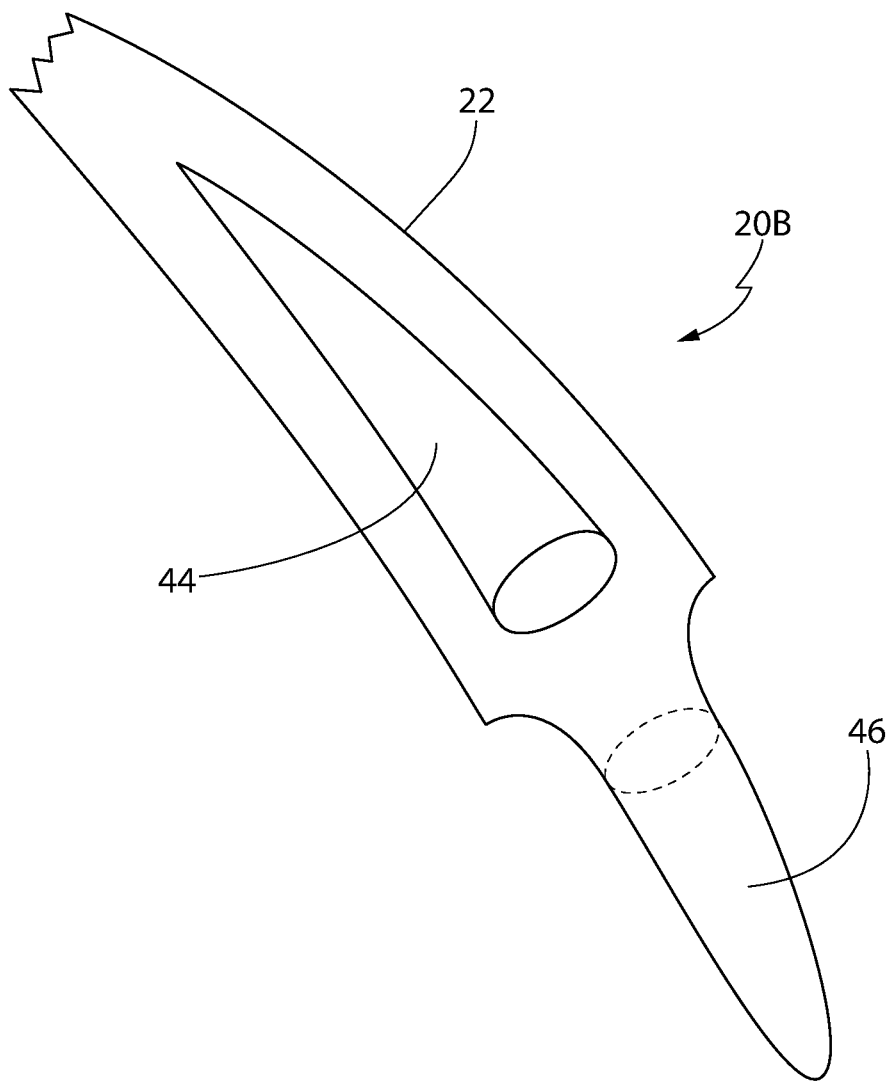
FIG. 2A is a partial isometric view of a second hair extension attachment apparatus of the invention.

FIG. 2A shows an isometric view of a second attachment apparatus 20B of the invention, wherein the apparatus comprises a protrusion element 46 and an attached extension element 22, and wherein the extension element 22 has a hollow core 44.

FIG. 2B shows a cross-sectional view of a hair anchor 1 and implant hair 2, wherein the implant hair 2 also comprises a hollow core 44.

FIG. 2C shows a cross-sectional view of the same hair implant of FIG. 2B, wherein the implant hair 2 is broken into two pieces at the point of hair breakage 30.

FIG. 2D shows the correction of the hair breakage in FIG. 2C by utilizing the second attachment apparatus 20B comprising an extension element 22 and the protrusion element 46 molded into a single embodiment. The protrusion 46 inserts into the hollow core 44 of the implant hair 2. The protrusion 46 may be held within the hollow core 44 through adhesive 42, friction, heating, or further chemical means.

Figure 3A:
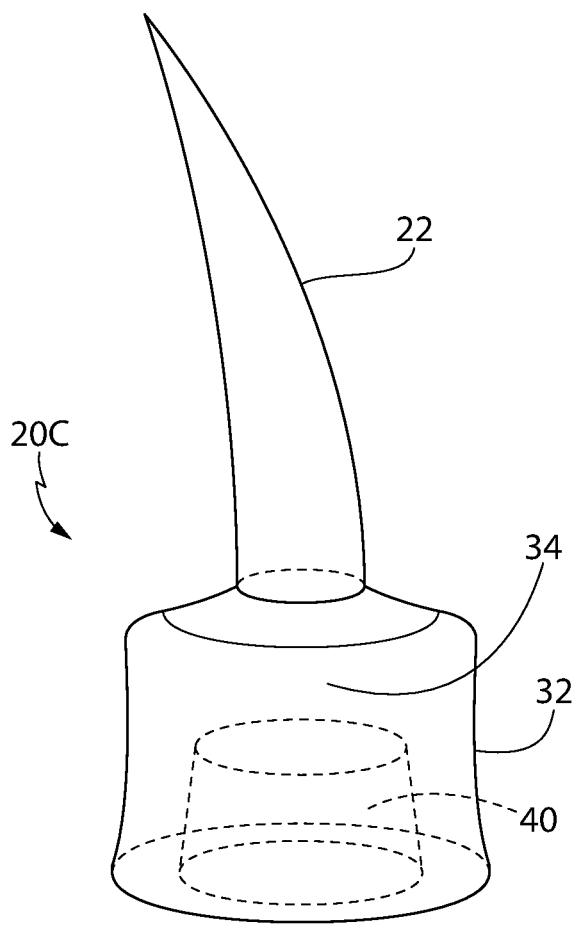
FIG. 3A is an isometric view of a third hair extension attachment apparatus of the invention.

FIG. 3A shows an isometric view of the third attachment apparatus of the invention, wherein the apparatus has a cylindrical outer appearance and comprises a core with solid vertical sides 32 connected at their distal ends by a solid horizontal component 34, forming a proximal cavity 40. A hair extension element 22 emerges from the horizontal component 34. It should be noted that there is no other cavity present in this embodiment.

Figure 3B:
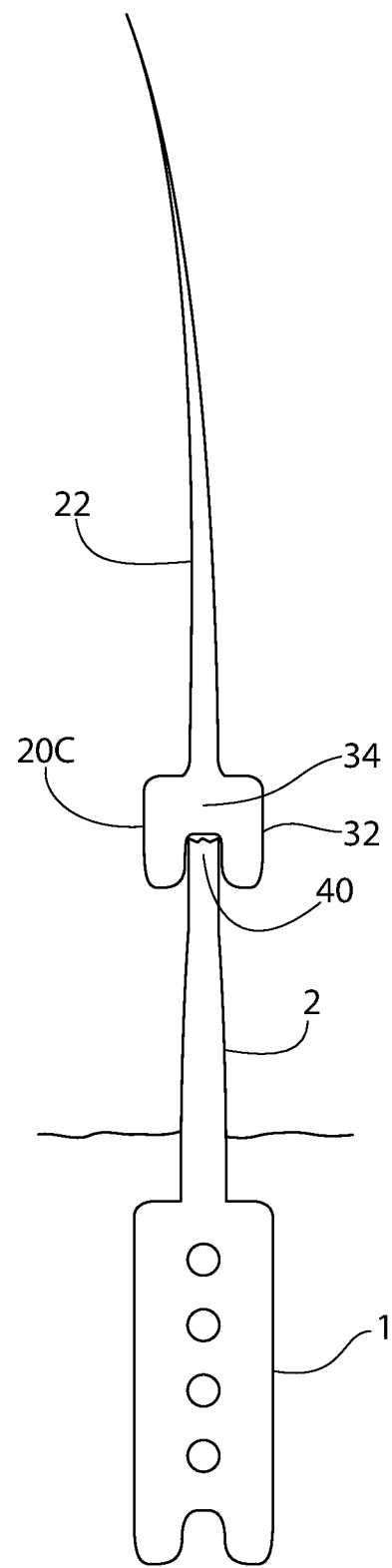
FIG. 3B is an enlarged, front view of a hair implant repair utilizing the third attachment apparatus of FIG. 3A.

FIG. 3B shows a front view of a hair implant utilizing an embodiment of the third attachment apparatus 20C of the invention. The third attachment apparatus 20C is attached to the implanted hair 2 by fitting the implanted hair inside the apparatus' cavity 40. The implanted hair 22/third apparatus 20C may be held in place via adhesive, heating, chemical means, or friction.

Figure 4:
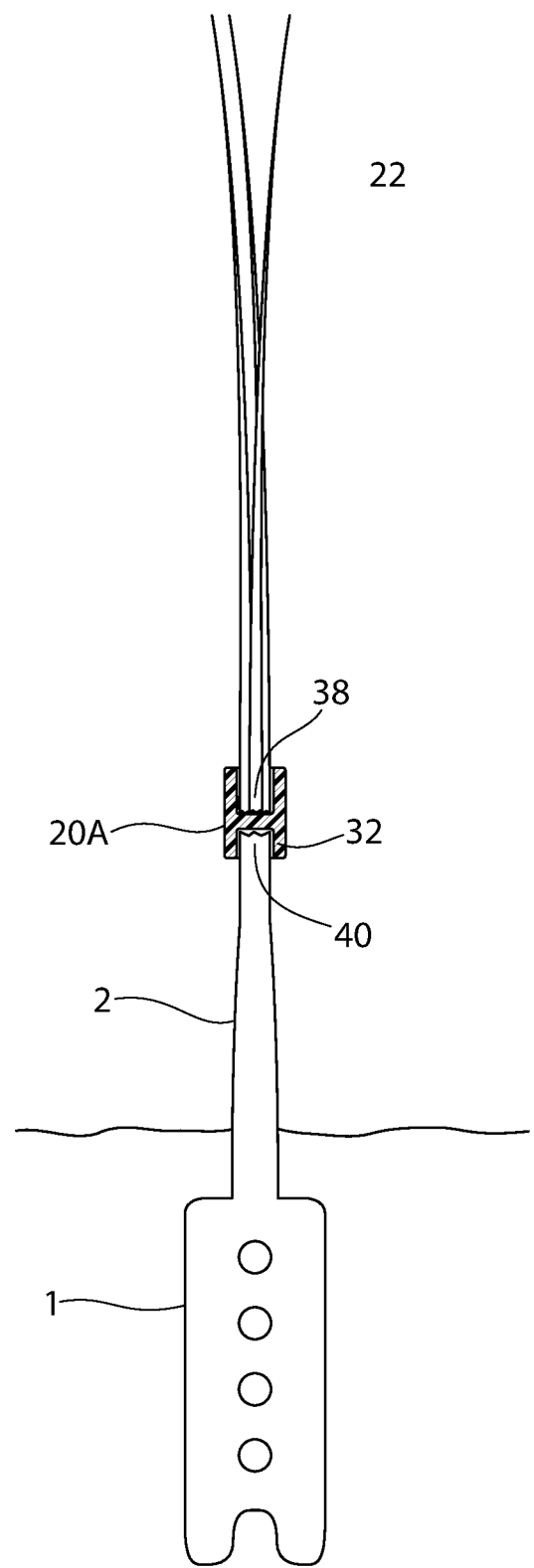
FIG. 4 is an enlarged front view of a hair implant utilizing a further embodiment of the first attachment apparatus of the invention.

FIG. 4 shows a front view of another embodiment of the first attachment apparatus 20A of the invention. An embodiment of the first attachment apparatus 20A is used to connect the implant hair 2 to a plurality of hair extension elements 22. This embodiment of the first attachment apparatus 20A allows multiple hair extension elements 22 to be inserted into the apparatus' distal cavity 38. The implant hair 2 is inserted into the proximal cavity 40. The vertical sides 32 are in contact with the sides of the implant hair 2 inside the proximal cavity 40 and with the sides of the plurality of extension elements 22 inside the distal cavity 38, thereby adding stability. The hair extension elements 22 may be inserted into the distal cavity 38 as a cluster or individually, each hair extension element 22 inserted into an individual, smaller distal subcavity (not shown). The hair implant 2 and extension elements 22 may be firmly held within the apparatus 20A through friction, heating, adhesive, or other chemical means.

Figure 5:
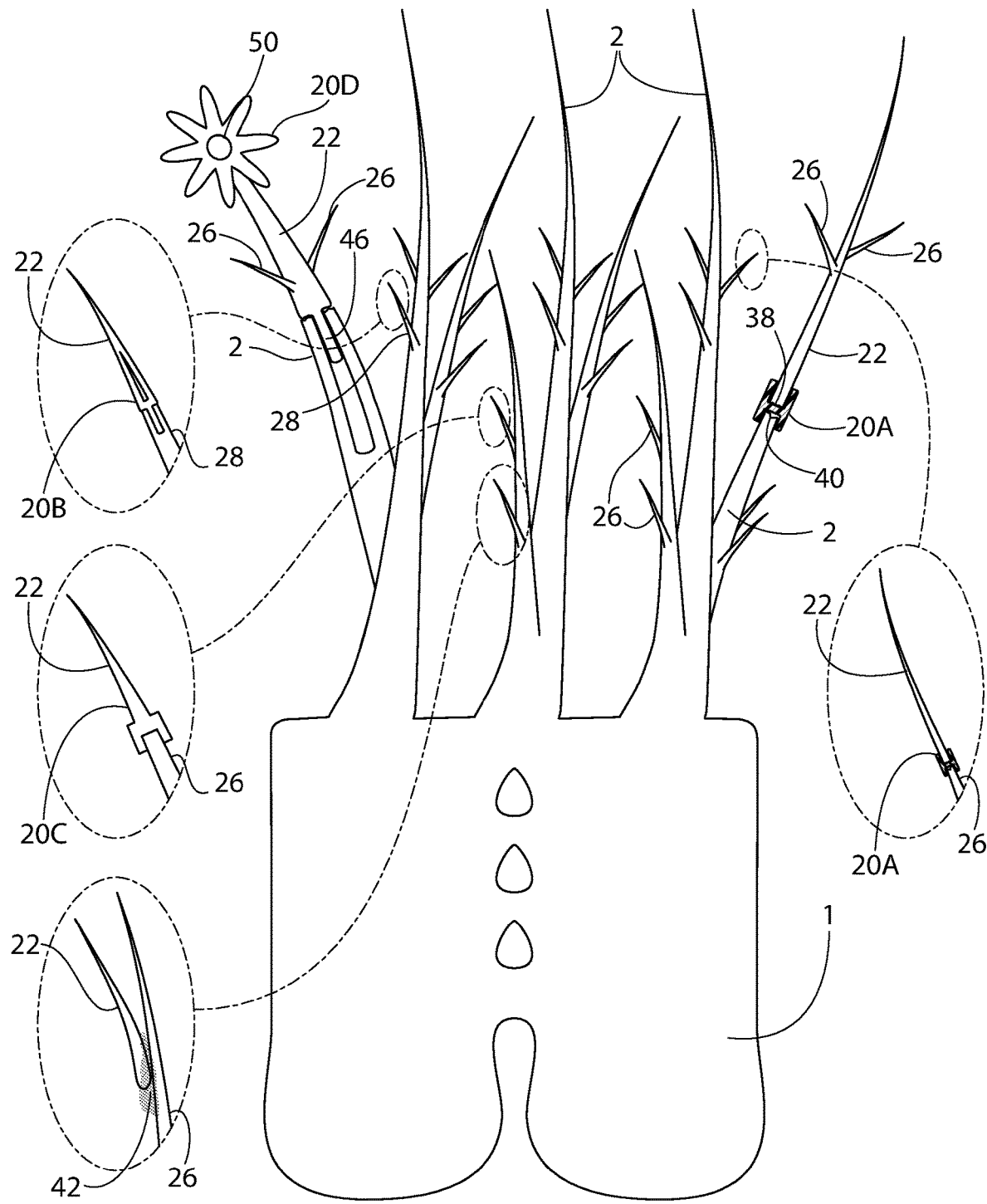
FIG. 5 is an enlarged front view of a hair implant comprising a plurality of hair elements, using the various extension attachments, and wherein bud structures, both solid and hollow, are also provided to serve as points of attachment for additional hair extensions to provide a more fuller hair look, if desired.

FIG. 5 shows a front view of an exemplary hair anchor 1 with a plurality of implant hairs 2 utilizing the extension apparatuses (e.g., apparatus 20A and apparatus 20B) of the invention, as described previously. In addition, to allow a more "fuller look of hair," buds 26 and 28 are also provided on the hair extension elements 2 or 22 to permit other hair extensions to be added thereto at a future time, as shown by the various insets in FIG. 5. In particular, the implant hair 2 itself, or the hair extension elements 22, may contain solid hair bud structures 26, small projections that serve as points of attachment for hair extension elements 22. An embodiment of the first attachment apparatus 20A may attach to the solid hair bud 26, with the bud 26 being inserted into the proximal cavity 40 of the apparatus 20A and the hair extension element 22 inserted into the distal cavity 38 of the apparatus 20A. Hollow hair buds 28 may also be present on the hair extension elements 22 or implant hairs 2 into which extensions with protrusions 46 may be inserted. Hollow hair buds 28 may also permit a fourth attachment apparatus 20D to be applied, wherein the protrusion 46 of the apparatus 20D is inserted into the hollow hair bud 28. The fourth attachment apparatus 20D comprises a hair extension element 22 having an ornamental structure 50, which may include but is not limited to flowers, beads, or feathers.

Figure 6:
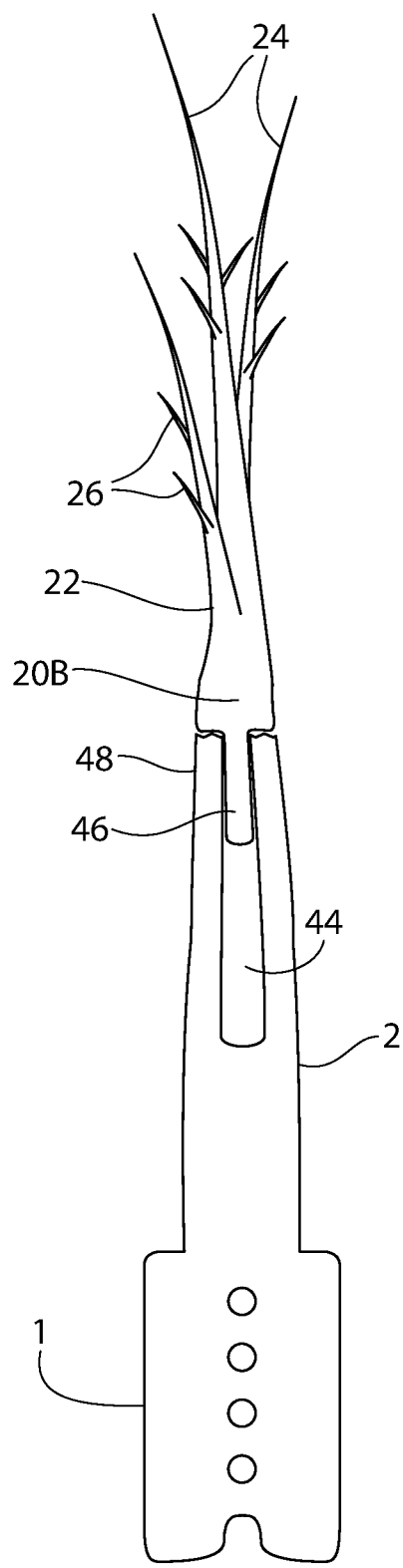
FIG. 6 is an enlarged front view of a hair implant utilizing a further embodiment of the second attachment apparatus of the invention.

FIG. 6 shows a front view of a further embodiment of the second attachment apparatus 20B of the invention. The utilized implant hair 2 comprises a hollow core 44, to which an extension 22 may be inserted into its distal end 48. The extension 22 may comprise a second attachment apparatus 20B complete with a protrusion 46 to be inserted into the distal end 48 of the implant hair 2 and remain inside the hollow core 44. The extension element 22 comprises both ancillary hair elements 24 permanently molded to the primary extension element hair 22 as well as hair bud structure 26 that can allow for the addition and removal of ancillary hairs as desired. The protrusion 46 may be adhered within the hollow core 44 of the implant hair element via adhesive, heating, friction, or other chemical means.

Figure 7:
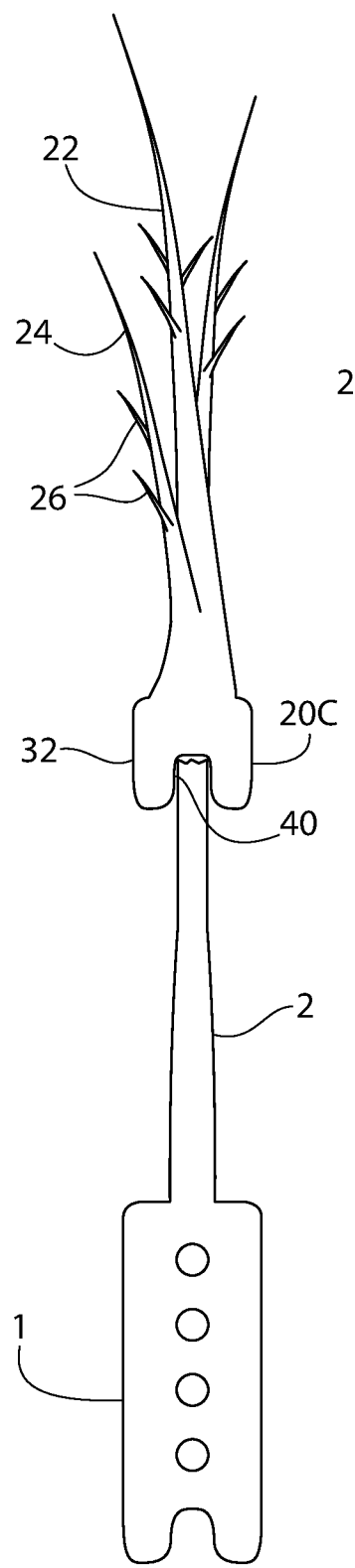
FIG. 7 is an enlarged front view of a hair implant utilizing a further embodiment of the third attachment apparatus of the invention.

FIG. 7 shows a front view of another embodiment of the third attachment apparatus 20C of the invention. As mentioned previously, the apparatus 20C comprises a single proximal cavity 40 and a primary extension strand 22 emerging from the apparatus. The primary extension strand comprises ancillary hairs 24 and hair buds 26 for optional addition and removal of the ancillary hairs. An implant hair 2 may be inserted into the proximal cavity 40. The inner vertical sides 32 of the attachment apparatus 20C are in parallel contact with the implant hair 2 for stability, and may be adhered to the implant hair 2 via adhesive, heating, friction, or other chemical means.

Figure 8:
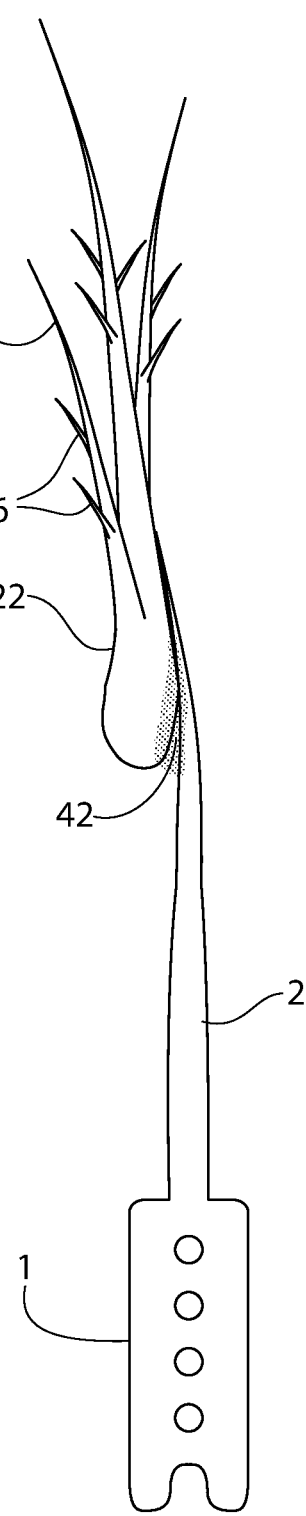
FIG. 8 is an enlarged front view of a hair implant utilizing a further embodiment a hair extension element.

FIG. 8 shows a front view of another embodiment of an extension apparatus of the invention. The extension 22 comprises ancillary hairs 24 and hair buds 26 for optional removal and addition of ancillary hairs. The end of the extension 22 overlaps with the end of the implant hair 2 and is fixed with adhesive 42. It is important to note that the hair extension element 22 of FIG. 8 utilizes no connector.

Attachment Technique

A primary concern with traditional hair extensions is the possibility of the extension falling out of the hair. When attempting to repair breakage of implanted hair or add length to the implanted hair, there is an added concern of placing stress on the hair anchor. The invention possesses features to lengthen the implant hair without causing damage to the existing implant.

The preferred attachment technique may include several attachment apparatuses, including but not limited to the first attachment apparatus 20A comprising vertical sides connected at a substantially central point by a horizontal component. As mentioned previously, the two cavities formed, one distal and one proximal, allow for the end of the broken or shortened implant strand to be inserted into the proximal concavity, while the end of the extension element(s) may be inserted into the distal cavity. The vertical sides come into parallel contact with the hairs, adding stability. Friction, heating, adhesive, or other chemical means may hold the hairs in place within the attachment apparatus.

As also mentioned previously, the second attachment apparatus may also be used, wherein the second attachment apparatus 20B comprises a proximal protrusion with an attached hair extension element or plurality of extension elements. This apparatus 20B is preferably utilized with implant hairs that possess internal hair chambers or hollow cores, as the protrusion from the attachment apparatus will insert into the hollowed space. The protrusion may be held in place within the hollow core through friction, heating, adhesive, or other chemical means. This particular attachment apparatus creates the appearance of a seamless strand of hair with no external protrusions.

Further techniques include but are not limited to a third attachment apparatus 20C, wherein vertical sides are connected at the top by a horizontal component. The hair extension strand(s) emerge from the horizontal component. Only a proximally facing cavity is formed by the structure, allowing the implant hair 2 to be inserted into the cavity. The implant hair can be secured in place via friction, heating, adhesive, or other chemical means.

For those wishing to add extensions with ornamental adornment including but not limited to flowers, beads, or feathers, an embodiment of the fourth attachment apparatus 20D may be utilized in which the ornamental feature is connected to the hair extension element 22 itself. The fourth attachment apparatus is preferably utilized with implant hairs with hollow cores or with hollow hair buds into which the protrusion may be inserted. The protrusion may be held in place via friction, heating, adhesive, or other chemical means.

Manufacturing of Implant Extensions

There are many types of hairs on the body including scalp, facial, eyebrow, arm and leg, pubic, eyelash, etc., and the manufacturing process can be modified to produce the appropriate hair implants for the skin area in question. Thus, for example, eyebrow hair implants will be smaller than scalp hair implants.

Implant extensions can be manufactured by a variety of different processes, including by injection molding and 3-D printing. The attachment apparatus preferably comprises a material selected for certain characteristics such as appropriate durometer, molecular weight, crosslinking, and strength. These characteristics help to provide the appropriate strength to withstand oxidation and fracturing during installation and daily activity.

In a preferred embodiment, medical grade silicone is used for attachment apparatus production. The silicone material is typically in a liquid form and in two parts. Upon mixing the two parts, part A and part B, a chemical reaction will occur and cause a silicone rubber to be formed. This liquid-to-solid reaction can be controlled by keeping the mixture cold to slow down the liquid-to-solid reaction and allow time to inject the liquid silicone into the mold. After being injected into the mold, heat is applied to complete the liquid-to-solid formation reaction.

The mold preferably comprises a multitude of cavities for receiving the liquid to be solidified to form the attachment apparatus components of the extension apparatus. The number of mold cavities is not particularly limited, and in certain embodiments can range from 1 or 10 or 100 or 1,000 or 10,000 cavities to 10 or 100 or 1,000 or 10,000 or 100,000 cavities per mold.

The fluid in the cavities should preferably be free of air bubbles, voids and the like. In certain embodiments, the anchor mold comprises two plates which are used in a process that minimizes or avoids air bubbles—a first plate having a plurality of holes through it and a second plate that closes off the holes in the first plate. The two plates are immersed in silicone liquid with the second plate being used to force the silicone liquid through the holes in the first plate (like a plunger on a syringe) until the two plates are in contact with each other. The excess silicone fluid is then scraped off the surface of the first plate to provide a mold having a plurality of cavities filled with substantially bubble-free liquid silicone.

In unitary hair extension attachment apparatuses of the invention (such as the second 20B or third attachment apparatus embodiments), hair strands are formed with or as a portion of the attachment apparatus using, e.g., molds including the attachment apparatus and hair and/or by drawing filaments from the attachment apparatus while it is still in an uncured state.

In non-unitary embodiments such as the first attachment apparatus embodiment, the strands of hair to be inserted in the attachment apparatuses are preferably pre-coated with silicone (or other bonding agent or primer compatible with silicone, such as alkoxy silane monomers or polymers as taught by U.S. Pat. No. 5,061,284 (Laghi), whose entire disclosure is incorporated by reference herein, to a length of, e.g., 2-10 mm or 6-8 mm or 7 mm, placed in the concavities, and then allowed to form a solid.

While the invention has been described in detail and with reference to specific examples thereof, it will be apparent to one skilled in the art that various changes and modifications can be made therein without departing from the spirit and scope thereof.

REFERENCES CITED (1) MEDLINEPLUS (2017). Hair loss. Medical Encyclopedia. MedlinePlus. https://medlineplus.gov/ency/article/003246.htm.
(2) INTERNATIONAL SOCIETY OF HAIR RESTORATION SURGERY (2003). Psychological effects of hair loss in women. http://www.ishrs.org/articles/hair-loss-effects.htm.
(3) KARAMAN et al. (2006). Androgenetic alopecia: Does its presence change our perceptions?. International journal of dermatology, 45(5), 565-568.
(4) BERNSTEIN, R. (2009) Psychological aspects of balding. https://www.bernsteinmedical.com/hair-loss/faq-myths-more/psychological-aspects-of-balding/.
(5) CASH, T. F. (1992). The psychological effects of androgenetic alopecia in men. Journal of the American Academy of Dermatology, 26(6), 926-931.
(6) MAPES, D. (2008). The fallout of hair loss: Suffering in silence. Skin and beauty. NBC News. http://www.nbcnews.com/id/26895411/ns/health-skin_and_beauty/t/fallout-hair-loss-suffering-silence/#.WaWCdMmYbF5.
(7) MEDLINE PLUS (2017). Hair loss. https://medlineplus.gov/hairloss.html.
(8) SINCLAIR et al. (2015). Androgenetic alopecia: new insights into the pathogenesis and mechanism of hair loss. F1000Research, 4(F1000 Faculty Rev): 585: 1-9.
(9) RAPOSIO et al. (2015). Scalp surgery: quantitative analysis of follicular unit growth. Plastic and Reconstructive Surgery Global Open, 3(10): 1-4.
(10) FIG. 1 of TEUMER et al. (2005, May). Follicular cell implantation: an emerging cell therapy for hair loss. In Seminars in Plastic Surgery (Vol. 19, No. 02, pp. 193-200).
(11) TOYOSHIMA et al. (2012). Fully functional hair follicle regeneration through the rearrangement of stem cells and their niches. Nature communications, 3, 784: 1-12.
(12) DUVERGER et al. (2014). To grow or not to grow: hair morphogenesis and human genetic hair disorders. Seminars in cell & developmental biology. Vol. 25: pp. 22-33.
(13) THIEDKE, C. C. (2003). Alopecia in women. American family physician, 67(5), 1007-1014.
(14) FOX et al. (2007). Traction folliculitis: an underreported entity. Cutis, 79(1), 26-30.
MIRMIRANI et al. (2014). Traction Alopecia. Dermatologic clinics, 32(2), 153-161.
(15) AVITZUR, O. (2013). The dangers of hair extensions: The beauty trend can cause headaches, baldness, and allergic reactions. Consumer Reports. https://www.consumerreports.org/cro/2013/02/the-dangers-of-hair-extensions/index.htm.
(16) AHDOUT et al. (2012). Weft hair extensions causing a distinctive horseshoe pattern of traction alopecia. Journal of the American Academy of Dermatology, 67(6), e294-e295.mpepe
(17) POSWAL et al. (2011). When FUE goes wrong!. Indian journal of dermatology, 56(5), 517-519.
(18) U.S. Patent Application No. 2009/0188512 (Eaton).
(19) U.S. Pat. No. 5,413,124 (Incando).
(20) U.S. Patent Application No. 2006/0065280 (Cheung).
(21) U.S. Patent Application No. 2003/0226571 (Rahman).

REFERENCE NUMBERS

1. Hair Anchor
2. Implant Hair
3. Epidermis
20A. First Attachment Apparatus
20B. Second Attachment Apparatus
20C. Third Attachment Apparatus
20D. Fourth Attachment Apparatus
22. Hair Extension Element
24. Ancillary Hair
26. Solid Hair Bud Structure
28. Hollow Hair Bud Structure
30. Point of Hair Breakage
32. Vertical Sides
34. Horizontal Component
36. Central Point
38. Distal cavity
40. Proximal cavity
42. Adhesive
44. Hollow Core
46. Protrusion
48. Distal End of Implant Hair
50. Ornamental Structure

What is claimed is:
1. A hair implant suitable for subcutaneous implantation within a patient, said hair implant comprising,
an anchor body having a plurality of apertures therethrough and wherein said anchor body is configured for subcutaneous implantation, said anchor body comprising at least two artificial hair elements that protrude from a distal end of said anchor body and wherein said at least two artificial hair elements are configured for projecting out of the epidermis of the patient;
at least one of said two artificial hair elements comprising ancillary hair elements and wherein said ancillary hair elements comprise bud structures thereon, said bud structures providing points of attachment for further hair extensions if desired; and wherein the other one of said at least two artificial hair elements comprises an extension apparatus for attaching a hair extension to a distal end of said other one of said at least two artificial hair elements.

2. The hair implant of claim 1 wherein said extension apparatus comprises:
a cylindrical structure having a first end with a first cavity therein and a second end with a second cavity therein; and
wherein said first cavity is configured to receive the distal end of said other one of said at least two artificial hair elements therein and said second cavity is configured to receive said hair extension therein.

3. The hair implant of claim 1 wherein said extension apparatus comprises:
a hair extension having a hair extension element forming a first portion of said hair extension and a projection forming a second portion, opposite said first portion, for being received inside a hollow interior of the said other one of said at least two artificial hair elements therein.

4. The hair implant of claim 3 wherein said hair extension element comprises a distal end having an ornamental structure thereon.

5. The hair implant of claim 4 wherein said ornamental structure comprises a flower-like design.

6. A method for forming a hair implant suitable for subcutaneous implantation within a patient, said method comprising,
forming an anchor body having a plurality of apertures therethrough and wherein said anchor body is configured for subcutaneous implantation;
forming at least two artificial hair elements that protrude from a distal end of said anchor body and wherein at least one said of two artificial hair elements is formed with ancillary hair elements having bud structures thereon, said bud structures providing points of attachment for further hair extensions if desired;
securing an extension apparatus, comprising the hair extension, to a distal end of the other one of said at least two artificial hair elements to join the hair extension on said other one of said at least two artificial hair elements.

7. The method of claim 6 wherein said step of securing comprises using friction, heat, adhesive or other chemical means for securing said extension apparatus to the distal end of said other one of said at least two artificial hair elements.

8. The method of claim 7 wherein said step of securing an extension apparatus comprises:
forming a cylindrical structure having a first end with a first cavity therein and a second end with a second cavity therein;
positioning a portion of said hair extension into said first cavity therein and securing said portion therein; and
positioning the distal end of the artificial implanted hair into said second cavity and securing the distal end therein.

9. The method of claim 8 wherein said step of securing said portion comprises using friction, heat, adhesive or other chemical means for securing said hair extension within said first cavity.

10. The method of claim 7 wherein said step of securing an extension apparatus comprises:
molding a hair extension element on a first end of a hair extension;
forming a projection at a second end, opposite said first end;
inserting said projection inside a hollow interior of said other one of said at least two artificial implanted hair elements; and
securing said projection inside the hollow interior of the said other one of said at least two artificial implanted hair elements.

11. The method of claim 7 wherein said step of securing an extension apparatus comprises:
molding a hair extension on first end of a hair extension core;
forming a single cavity on a second end, opposite said first end, of said core;
inserting the distal end of the other one of said at least two artificial implanted hair elements within said single cavity; and
securing said distal end inside said single cavity.

* * * * *